(12) United States Patent
Larsen et al.

(10) Patent No.: US 6,184,216 B1
(45) Date of Patent: Feb. 6, 2001

(54) AMINOGUANIDINE CARBOXYLATE LACTAMS FOR THE TREATMENT OF NON-INSULIN-DEPENDENT DIABETES MELLITUS

(75) Inventors: Scott D. Larsen; Martin D. Meglasson; Valerie A. Vaillancourt, all of Kalamazoo; Paul D. May, Richland, all of MI (US)

(73) Assignee: Pharmacia & Upjohn Company, Kalamazoo, MI (US)

( * ) Notice: Under 35 U.S.C. 154(b), the term of this patent shall be extended for 0 days.

(21) Appl. No.: 09/307,135

(22) Filed: May 7, 1999

Related U.S. Application Data

(62) Division of application No. 08/857,760, filed on May 15, 1997, now Pat. No. 5,955,617.
(60) Provisional application No. 60/017,679, filed on May 21, 1996.
(51) Int. Cl.[7] ............... A61P 3/04; A61P 3/10; C07D 205/04; C07D 229/00
(52) U.S. Cl. ............ 514/210.02; 540/202; 540/362
(58) Field of Search ............ 514/210.02; 540/202, 540/362

(56) References Cited

U.S. PATENT DOCUMENTS

| | | | |
|---|---|---|---|
| 3,412,105 | 11/1968 | Langis | 260/349.5 |
| 4,789,681 | 12/1988 | Sportoletti et al. | 514/392 |
| 5,132,453 | 7/1992 | Griffith | 512/560 |
| 5,272,165 | 12/1993 | Ulrich et al. | 514/357 |
| 5,360,925 | 11/1994 | Lassauniere et al. | 560/169 |
| 5,480,999 | 1/1996 | Lassauniere et al. | 548/500 |
| 5,691,356 * | 11/1997 | Das et al. | 514/326 |

FOREIGN PATENT DOCUMENTS

| | | |
|---|---|---|
| 0531812 | 8/1992 | (EP) . |
| 54-128590 | 10/1979 | (JP) . |
| WO 8910701 | 11/1989 | (WO) . |
| WO 9104023 | 4/1991 | (WO) . |
| WO 9419335 | 9/1994 | (WO) . |
| WO 9616031 | 5/1996 | (WO) . |

OTHER PUBLICATIONS

Gante, J., *J. Chem. Ber.*, 101:1195–1199 (1986).
Chem Abstract 92:75899h (1980).
Chem. Abstract 113:39340n (1990).
Chem Abstract 92:46819v (1980).
* cited by examiner

*Primary Examiner*—Bruck Kifle
(74) *Attorney, Agent, or Firm*—Dinsmore & Shohl LLP

(57) ABSTRACT

Compounds selected from the group consisting of formulae III, IV, VI and VIII

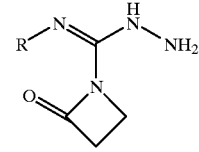

(III)

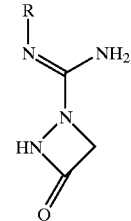

(IV)

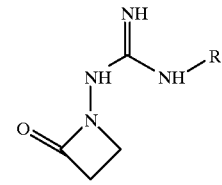

(VI)

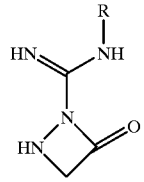

(VII)

wherein R is H is NH$_2$, or a pharmacologically acceptable salt thereof, are suitable for use in methods for treating non-insulin-dependent diabetes mellitus (NIDDM) or obesity in a patient susceptible to or experiencing NIDDM or obesity by the systemic administration of such a compound in an amount effective to treat the NIDDM or obesity.

10 Claims, No Drawings

AMINOGUANIDINE CARBOXYLATE LACTAMS FOR THE TREATMENT OF NON-INSULIN-DEPENDENT DIABETES MELLITUS

CROSS-REFERENCE TO RELATED APPLICATIONS

This is a divisional of application Ser. No. 08/857,760 filed May 15, 1997, now U.S. Pat. No. 5,955,617. This application claims the benefit of provisional application Ser. No. 60/017,697, filed May 21, 1996, under 35 USC 119(e)(i).

BACKGROUND OF THE INVENTION

The present invention provides novel compounds and a novel method for treating: non-insulin dependent diabetes mellitus (NIDDM); impaired glucose tolerance; and obesity.

Non-insulin dependent diabetes mellitus, or NIDDM, and Type II diabetes are synonymous. NIDDM patients have an abnormally high blood glucose concentration when fasting and delayed cellular uptake of glucose following meals or after a diagnostic test known as the glucose tolerance test. NIDDM is diagnosed based on recognized criteria (American Diabetes Association, Physician's Guide to Insulin-Dependent (Type I) Diabetes, 1988; American Diabetes Association, Physician's Guide to Non-Insulin-Dependent (Type II) Diabetes, 1988).

Impaired glucose tolerance occurs when the rate of metabolic clearance of glucose from the blood is less than that commonly occurring in the general population after a standard dose of glucose has been orally or parenterally administered (American Diabetes Association, Physician's Guide to Non-Insulin-Dependent (Type II) Diabetes, 1988). Impaired glucose tolerance can occur in NIDDM, insulin dependent diabetes mellitus, middle age onset diabetes mellitus of the young, gestational diabetes and obesity. Impaired glucose tolerance can also occur in individuals not meeting the diagnostic criteria for these disease states. Impaired glucose tolerance in non-diabetic individuals is a predisposing factor for the development of NIDDM.

Obesity is a condition in which there is an increase in body fat content resulting in excess body weight above the accepted norms for age, gender, height, and body build (Bray, Obesity, An Endocrine Perspective, p. 2303, Multihormonal Systems and Disorders (1989)). Accepted norms have been determined by life insurance mortality experience and by incidence of morbidity in relation to body composition. The excess mortality that occurs in obese individuals results from diseases that are predisposed by this condition. They include cancer, cardiovascular disease, digestive disease, respiratory disease and diabetes mellitus.

In patients with chronic hyperglycemia such as occurs in non-insulin dependent diabetes, glucose-dependent protein crosslinking occurs at a rate in excess of the norm (Bunn, American Journal of Medicine, Vol. 70, p. 325, 1981) resulting in altered tertiary protein structure (Brownlee, Chapter 18, Diabetes Mellitus, p. 279, 1990). Excessive non-enzymatic glycosylation of proteins contributes to diabetic complications and complications of aging in non-diabetic humans, such as neuropathy, nephropathy, retinopathy, hypertension, and atherosclerosis (Brownlee, 1990, supra).

Hyperglycemia is defined as blood glucose concentration in excess of the accepted norm for the general population (American Diabetes Association, Physician's Guide to Non-Insulin-Dependent (Type II) Diabetes, 1988).

Reducing the abnormally high blood glucose level of diabetic subjects benefits the patient by reducing the discomfort of glycosuria and the excessively high mortality and morbidity associated with diabetes mellitus (Kahn, Diabetes Mellitus Theory and Practice, 4th ed., Chapter 26, p. 450, 1990). Weight loss by patients with diabetes mellitus who are obese results in a long-term reduction of the excessively high blood glucose level (Wing, Archives of Internal Medicine, Vol. 147, p. 1749, 1987; Kahn, Diabetes Mellitus Theory and Practice, 4th ed., Chapter 26, p. 450, 1990). As a result of this beneficial effect of weight loss on diabetes mellitus, weight reduction is the treatment of choice for obese patients with diabetes (Karam, Chapter 33, Diabetes Mellitus and Obesity, p. 298, 1982). While the relationship between diabetes mellitus and obesity is known, it would be an advantage to have a drug which can treat or prevent both of them.

INFORMATION DISCLOSURE 3-(1-(Aminomethyl)hydrazino)) propanoic acid is reported in JP 54128523 (Chem. Abstr. 92:75899h) to be a fungicide and insecticide. The synthesis of N-(hydrazinoiminomethyl)-glycine is reported in: Gante, *J. Chem. Ber.* 1968,101, 1195. Certain alkylidene-amino guanidine derivatives are described in U.S. Pat. No. 5,272, 165 titled "Inhibiting advanced glycosylation of body proteins—using 2-alkylidene-amino:guanidine deriv., used e.g. for treating diabetic side-effects or esp. preventing tooth staining." Aminoguanidine analogs of arginine are disclosed in DE 4244539-A1 and WO 9104-023-A. U.S. Pat. No. 5,132,453 discloses that N6-(hydrazino:imino:methyl)-lysine is useful as an inhibitor of nitric oxide formation and for treating hypertension. EP-230-037-A discloses certain new 2-substituted-guanidine derivatives having antiischaemic and cardioprotective activity. U.S. Pat. No. 3,412, 105 discloses P-Aryl-N-guanidino-(β-alanines or α-carboxy-β-alanines) as MAO inhibitors and long acting hypotensives. "Aminoguanidine carboxylates for the treatment of NIDDM" are disclosed in U.S. application Ser. No. 95/14126. Cyclic aminoguanidine carboxylates are disclosed in "Preparation and formulation of hydrazonothiazoles and imidazoles as physiological Maillard reaction inhibitors" (WO 9419335 A1, *Chem. Abstr.* 122:314548).

The preparation of certain α-hydrazonoimidazolidin-4-ones, -thiazolidine-4-ones and related compounds as Maillard reaction inhibitors is described in EP 531,812. The preparation of certain uracil derivatives is described in WO 89/10,701. Kokai Tokkyo Koho 79,128,590 describes certain 3-amino-5-hydroxy-6,7-dihydro-1[H]-1,2,4-triazepines.

SUMMARY OF THE INVENTION

The present invention particularly provides:

(1) A compound of the formulae I–VIII:

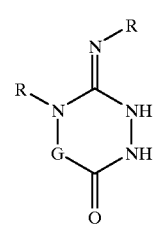

I

-continued

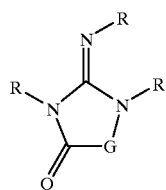
II

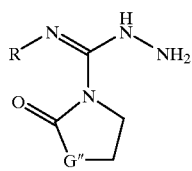
III

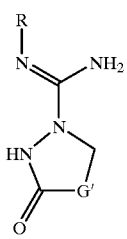
IV

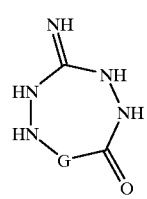
V

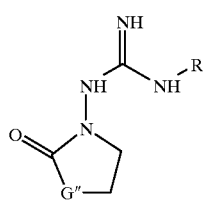
VI

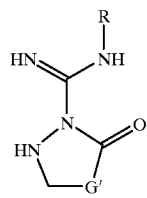
VII

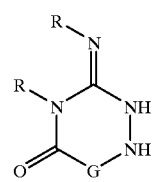
VIII or a pharmacologically acceptable salt thereof,
wherein G is $(CH_2)_n$;
wherein G' is $(CH_2)_m$;
wherein G'' is $(CH_2)_p$;
wherein R is H or $NH_2$;
wherein n is an integer from 1–5;
wherein m is an integer from 0–4;
wherein p is an integer from 0–3;
with the proviso that in formulae II, at least one R group must be $NH_2$, and when G is $(CH_2)_1$, formula II excludes the structure represented by formula XI

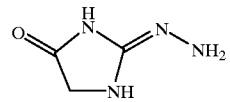

with the proviso that in formula I, when G is $(CH_2)_1$ at least one R group must be $NH_2$;
with the proviso that in formula VIII, when G is $(CH_2)_2$ at least one R group must be $NH_2$.

(2) a method for treating or preventing non-insulin dependent diabetes mellitus or obesity in a patient susceptible to or experiencing said NIDDM or obesity comprising the systemic administration of an amount effective to treat or prevent NIDDM or obesity of a compound of the formulae IX–XI.

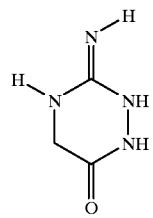
IX

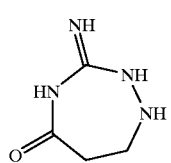
X

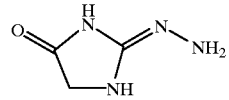
XI

Examples of pharmaceutically acceptable acid addition salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate.

The dose of compounds of formula I–VIII to be used is between 0.1 and 100 mg/kg body weight daily. The preferred dose is 1–50 mg/kg/day. Administration may be by oral, parenteral, intranasal, buccal, sublingual, intrarectal, or transdermal routes. The oral route is preferred.

Novel compounds of the invention are given by the generic formulae I–VIII. Known compounds claimed for use in the treatment of NIDDM are represented by formula IX–XI.

Of the compounds of this invention, represented by generic formulae I–VIII, the compounds listed in Table 1 are especially preferred and their preferred utility is in the treatment of NIDDM and its complications. Procedures for their preparation are given in Section 4. Table 2 contains a list of compound specifically claimed by this invention.

Thus, the present invention provides novel and known compounds having surprising and unexpected antidiabetic properties. Administration of the compounds of this invention to KKAy mice at a dose of approximately 100–500 mg/kg/day results in the partial or complete amelioration of hyperglycemia in this rodent model of non-insulin dependent diabetes mellitus (Specific compounds are listed in Tables 1 and 2; see Chang, Wyse, Copeland, Peterson, and Ledbetter, Diabetes 1985, p. 466, 1986). KKAy mice are insulin resistant (Chang, et al, supra) and the finding that the non-fasting blood glucose level is reduced in these animals indicates that insulin resistance is most probably less after treatment with the claimed compounds. KKAy mice are obese compared to normal, outbred mice (Chang, et al, supra) and administration of compounds of the invention results in weight loss.

Administration of 4-imidazolidinone, 1,3-diamino-2-imino-, monohydrochloride, the most preferred compound in this series, to diabetic KKAy mice for 3 days decreased the non-fasting blood glucose level of the animals (see Table 3). A dose of 125 mg/kg/day produced a decrease in the blood glucose level that was approximately equal to the effect of 3-Guanidinopropionic acid at 700 mg/kg/day. A higher dose of 4-imidazolidinone, 1,3-diamino-2-imino-, monohydrochloride produced an even greater reduction in the blood glucose concentration.

Administration of 4-imidazolidinone, 1,3-diamino-2-imino-, monohydrochloride to obese KKAy mice for 3 days decreased the body weight of the animals (see Table 3). A dose of 125 mg/kg/day produced a -1.90% decrease in the body weight compared to the control mice. A higher dose of 4-imidazolidinone, 1,3-diamino-2-imino-, monohydrochloride produced an even greater reduction in the body weight of obese mice.

Administration of a variety of related structural analogs of 4-imidazolidinone, 1,3-diamino-2-imino-, monohydrochloride to diabetic, obese KKAy mice for 3 days resulted in a reduction in the abnormally elevated blood glucose of these mice or a decrease in the excessive body weight of the animals (Table 4). 4-Imidazolidinone, 1,3-diamino-2-imino-, monohydrochloride and a mixture of 1,2,4-triazine-3,6-dione, tetrahydro-, 3-hydrazone, monohydrochloride and 2,4-imidazolidinedione, 3-amino-, 2-hydrazone, monohydrochloride caused both the blood glucose and body weight to decrease. 1,2,4-triazin-5(2H)-one, 3-amino-1,6-dihydro-, monohydrochloride and 1,2,4-triazine-3,5(2H,4H)-dione, dihydro-, 3-hydrazone, monohydrochloride caused a reduction in body weight. The blood glucose level did not decrease with these compounds during the 3 day experiment. Since the mean blood glucose level in obese diabetic humans decreases when body weight is reduced for 12, 36, or 64 weeks (Wing, Archives of Internal Medicine, Vol. 147, p. 1749, 1987), the weight reduction with 1,2,4-triazin-5(2H)-one, 3-amino-1,6-dihydro-, monohydrochloride and 1,2,4-triazine-3,5(2H,4H)-dione, dihydro-, 3-hydrazone, monohydrochloride should cause improvement in the hyperglycemic state with longer term administration.

In patients with diabetes mellitus, there are several metabolic disorders that would be of therapeutic benefit to correct: the abnormally elevated blood level of glucose in the fed and fasted states, the delayed clearance of glucose from the blood stream (American Diabetes Association, Physician's Guide to Insulin-Dependent (Type I) Diabetes, 1988; American Diabetes Association, Physician's Guide to Non-Insulin-Dependent (Type II) Diabetes, 1988), and the excessive glycosylation of proteins which contributes to the development of diabetic complications (Brownlee, supra). Furthermore, obesity is frequently associated with non-insulin dependent diabetes mellitus and aggravates the disordered glucose metabolism in these patients (Horton and Jeanrenaud, Chapter 27, Obesity and Diabetes Mellitus, 1990). The optimal treatment for non-insulin dependent diabetes mellitus would correct all of these disorders, but in particular would correct obesity (Karam, Chapter 33, Diabetes Mellitus and Obesity, p. 298, 1982; Kahn, Diabetes Mellitus Theory and Practice, 4th ed., Chapter 26, p. 450, 1990). Excessive glycosylation of proteins, such as can occur in non-insulin dependent diabetes mellitus, can be prevented by reducing the abnormal elevation of blood glucose concentration in the diabetic state (Holman and Turner, Diabetic Medicine, 5:582–588, 1988; Benjamin and Sacks, Clin Chem., 4015:683–687, 1994).

It is the ability of the claimed compounds to positively affect multiple metabolic defects comprising diabetes mellitus and to prevent metabolic defects by more than one mechanism that clearly distinguishes their pharmacologic actions from other guanidine compounds that have previously been claimed as treatments for diabetes mellitus. The claimed compounds are unexpectedly superior to aminoguanidine, diaminoguanidine, 3-guanidinopropionic acid, and metformin in the treatment of NIDDM because they offer a more complete spectrum of desirable activities or are effective in lower doses.

The claimed compounds offer unexpected advantages in the treatment of diabetes mellitus compared to diaminoguanidine and aminoguanidine since the claimed compounds act metabolically to reduce excessive blood glucose concentration. The claimed compounds are unexpectedly superior to aminoguanidine and diaminoguanidine in the treatment of impaired glucose tolerance or obesity since aminoguanidine and diaminoguanidine lack efficacy in this regard. Aminoguanidine and diaminoguanidine inhibit non-enzymatic glycosylation of proteins in vitro and the formation of advanced glycosylation endproducts in vivo (Kumari, Umar, Bansal, and Sahib, Diabetes, 40:1079–1084, 1991). Based on its inhibition of nonenzymatic protein glycosylation, aminoguanidine has been suggested to have utility in the treatment of diabetes (Brownlee, supra).

Aminoguanidine has no effect on the blood glucose level of normal rodents or rats made diabetic by injection of alloxan or streptozotocin (Kumari, Umar, Bansal, Sahib, supra; Yagihashi, Kamijo, Baba, Yagihashi, and Nagai, Diabetes, 41:47–52, 1992; Edelstein and Brownlee, Diabetologia, 35:96–97, 1992; Oxlund and Andreassen, Diabeterologia, 35:19–25, 1992). Diaminoguanidine has no effect on the blood glucose level of normal or alloxan-diabetic rats (Kumari, Umar, Bansal, Sahib, supra). Aminoguanidine has no effect on the body weight of normal or diabetic rats (Kumari, Umar, Bansal, Sahib, supra; Yagihashi, Kamijo, Baba, Yagihashi, and Nagai, supra: Oxlund and Andreassen, Diabetologia, 35:19–25, 1992) or results in an increase in body weight of human and rats (Baylin, Horakova, and Beaven, Experientia, 31:562, 1975). Diaminoguanidine does not affect the body weight of normal or alloxan-diabetic rats (Kumari, Umar, Bansal, Sahib, supra). An effect by aminoguanidine or diaminoguanidine on glucose tolerance has yet to be demonstrated.

The claimed compounds are unexpectedly superior to 3-guanidinopropionic acid in the treatment of diabetes mellitus since the latter is less potent in the control of hyperglycemia. 3-Guanidinopropionic acid has previously been shown to reduce hyperglycemia and excess body weight and to improve glucose tolerance in diabetic rodents (Meglasson, Wilson, Yu, Robinson, Wyse, and de Souza, J. Pharm. and Exp. Therapeutics, 266:1454–1462, 1993). The most preferred compound in this claim, 4-imidazolidinone, 1,3-diamino-2-imino-, monohydrochloride, is more potent than 3-guanidinopropionic acid in reducing the abnormally elevated blood glucose level of KKAy mice. To reduced the blood glucose level of KKAy mice by 35% required 700 mg/kg/day of the latter compound. A similar reduction in the blood glucose level could be achieved with a dose of 125 mg/kg/day of 4-imidazolidinone, 1,3-diamino-2-imino-, monohydrochloride.

The claimed compounds are unexpectedly superior to metformin in the treatment of diabetes mellitus, glucose intolerance, and obesity since the latter is less potent when tested in the same animal model as the claimed compounds. Also, with respect to its efficacy in reducing body weight, the disclosed data for metformin are contradictory and do not reveal a consistent result. Metformin has previously been shown to reduce hyperglycemia in non-insulin dependent diabetic patients when administered at 1000–3000 mg/day and to increase the rate of glucose clearance in such patients when administered at 1500–2500 mg/day (Bailey, Diabetes Care, 15:755–772, 1992). Rodents are less sensitive to metformin than humans and therefore higher doses (based on body weight) are required to demonstrate glycemic effects (Bailey, Flatt, Wilcock, and Day, Frontiers in Diabetes Research, pp. 277–282, 1990; Penicaud, Hitier, Ferre, and Girard, Biochem. J. 262:881–885, 1989). Chronic oral administration of metformin reduces hyperglycemia when administered to neonatal streptozotocin-diabetic rats at 100 mg/kg/day (Rossetti, DeFronzo, Gherzi, Stein, et al, Metabolism, 39:425–435, 1990), to DBM mice at 400 mg/kg/day (Bailey, Flatt, Wilcock, and Day, supra), to Zucker fa/fa rats at 350 mg/kg/day (Penicaud, Hitier, Ferre, and Girard, supra), and to KKAy mice at 300 mg/kg/day or more (Meglasson, Wilson, Yu, Robinson, de Souza, supra). Chronic oral administration of metformin did not affect the blood glucose concentration in normal mice receiving 250 mg/kg/day, in streptozotocin-diabetic mice receiving 250 mg/kg/day (Bailey, Flatt, Wilcock, and Day, supra), or diabetic ob/ob mice receiving 250 mg/kg/day (Bailey, Flatt, and Ewan, Arch. Int. Pharmacodyn., 282:233–239, 1986). Acute administration of 264 mg/kg metformin or its analog buformin at 132 mg/kg did not affect the blood glucose level of rats (Tutwiler and Bridi, Diabetes, 27:868–876, 1978). When the most preferred compound in this claim, 4-imidazolidinone, 1,3-diamino-2-imino-, monohydrochloride, was tested in KKAy mice it was more potent than metformin in reducing the abnormally elevated blood glucose level in this model. To reduce the blood glucose level of KKAy mice by 25% required 300 mg/kg/day of metformin (Meglasson, Wilson, Yu, Robinson, Wyse, and de Souza, supra). A similar reduction in the blood glucose level could be achieved with a dose of 70–125 mg/kg/day of 4-imidazolidinone, 1,3-diamino-2-imino-, monohydrochloride. With respect to increasing glucose tolerance metformin has been reported to not affect glucose tolerance in normal rats when given at a dose of 750 mg/kg (Tutwiler and Bridi, supra) or in normal mice when given at 50 mg/kg (Bailey, Flatt, Wilcock, and Day, supra). When given to normal mice or streptozotocin-diabetic rats at 250 mg/kg oral glucose tolerance was increased (Bailey, Flatt, Wilcock, and Day, supra). With respect to reducing body weight, metformin has been reported to cause weight loss in non-insulin dependent diabetic patients treated for one year (Bailey, supra) or to have no significant effect on the body weight of obese non-insulin dependent diabetic patients treated for a similar length of time (Multi-centre Study, Diabetologia, 24:404–411, 1983). Metformin did not cause weight loss in diabetic ob/ob mice when administered at 240 mg/kg/day or streptozotocin-diabetic mice when administered at 60 mg/kg/day (Lord, Atkins, and Bailey, Diabetologia 25:108–113, 1983). Metformin caused statistically significant weight loss in KKAy mice treated with 1700 mg/kg/day of the compound, but not when lower doses were given (Meglasson, Wilson, Yu, Robinson, Wyse, and de Souza, supra). By comparison, when N-(dihydrazinomethylene)glycine was administered to KKAy mice at 100 mg/kg/day it was approximately as effective as 1700 mg/kg/day of metformin in producing weight loss in this obese mouse strain (Meglasson, Wilson, Yu, Robinson, Wyse, and de Souza, supra).

General methods for the preparation of the compounds of this invention are represented by the specific reactions in Schemes 1–4. Specific examples of these techniques can be found in the experimental procedures presented in the Description of the Preferred Embodiment. By using other starting materials the various compounds of the invention may be prepared. The following references discuss procedures relating to the general syntheses of the compounds of this invention or intermediates required for the syntheses thereof.

Scheme 1: Gut, J.; Hesoun, D; Novacek, A. *Coll. Czech. Chem. Comm.* 1966, 31, 2014.

Scheme 2: Bierowska-Charytonowics, D.; Konieczny, M. *Rocz. Chem.* 1973, 47, 99.

Schemes 3 and 4: U.S. Ser. No. 95/14126.

Specific references to known compounds of formulae IX–XI are provided in: Svetkin, Y V; Minlibaeva, A. N. *Chem. Abstr.* 89:43345 (1978); Shirai, K; Kumamoto, T.; Kobayashi, Y.; Ri, T. JP 78-35581 (*Chem. Abstr.* 92:146819); "Cephalosporin derivatives with bactericidal activity", NL 7507539, *Chem. Abstr.* 87:201565; "Cephalosporins", DE 75-2525840, *Chem. Abstr.* 86:155677.

DESCRIPTION OF THE PREFERRED EMBODIMENTS

The following experimental procedures are specific examples which describe the reparation of a number of compounds of the invention:

EXAMPLE 1

1,2,4-Triazin-5(2H)-one, 3-amino-1,6-dihydro-, monohydrochloride (Compound 4)

A solution of aminoguanidine bicarbonate (13.5 g, 91.5 mmol), conc. HCl (30 L) and water (70 mL) was mixed with chloral hydrate (16.5 g, 11.2 mmol). The resulting solution was refluxed for 1 h. The reaction was condensed to half volume at which time a white precipitate was formed. The reaction was cooled and filtered. The crude solid was recrystallized from 3N HCl to yield 9.66 g (52%) of 2 as a white crystalline solid. MP: 185–188° C. $^1$H NMR (D$_2$O):δ 7.50 (s, 1H). Anal calcd for C$_3$H$_8$N$_4$O$_2$.HCl.H$_2$O: C, 19.51; H, 4.88; N, 30.35. Found: C, 19.47; H, 4.89; N, 30.54.

A suspension of 2 (3.00 g, 23.1 mmol) in water (100 mL) was stirred at reflux for 48 h (material had gone into solution after 24 h). After 48 h, the reaction was cooled to room temperature. A yellow precipitate was collected and recrystallized from water. This material was recrystallized from MeOH/H$_2$O to yield 3 (1.30 g, 50%) as a yellow crystalline solid. MP: >290° C. $^1$H NMR (DMSO-d$_6$):δ 12.31 (bs, 1H), 7.34 (s, 1H), 6.98 (bs, 2H). Anal calcd for C$_3$H$_4$N$_4$O: C, 32.14; H, 3.57; N, 50.00. Found: C, 31.98; H, 3.56; N, 50.14.

A solution of 3 (1.65 g, 14.7 mmol) in H$_2$O (40 mL) and conc. HCl (8 mL) was hydrogenated over 10% Pd/C (165 mg) at 40 psi for 1.5 h. The reaction mixture was filtered and the filtrate concentrated in vacuo. The residue was recrystallized from MeOH to yield 4 (1.48 g, 68%) as a white solid. MP: 204–205° C. (dec). $^1$H NMR (CD$_3$OD):δ 3.60 (s, 2H). Anal calcd for C$_3$H$_6$N$_4$O.HCl: C, 24.16; H, 4.70; N, 37.58; Cl, 23.49. Found: C, 23.88; H, 4.39; N, 37.23; Cl, 23.44.

EXAMPLE 2

1,2,4-Triazine-3,5(2H, 4H)-diene, dihydro-, 3-hydrazone, monohydrochloride (Compound 7)

To a solution of 1,3-diaminoguanidine hydrochloride (5.00 g, 39.8 mmol) in water (29 mL) and conc. HCl (12 mL) was added glyoxylic acid monohydrate (4.15 g, 45.1 mmol). The reaction was stirred at reflux for 1 h and then cooled to room temperature. The reaction mixture was concentrated to half volume The precipitate was collected and recrystallized twice from MeOH to yield 6 (2.37 g, 37%) as a white crystalline solid. MP: 242–244° C. $^1$H NMR (DMSO-d$_6$):δ 9.00 (bs, 1H), 7.79 (s, 1H), 5.60 (bs, 1H). Anal calcd for C$_3$H$_5$N$_5$O.HCl: C, 22.09; H, 3.68; N, 42.94; Cl, 21.47. Found: C, 21.84; H, 3.83; N, 42.61; Cl, 21.43.

A solution of 6 (3.00 g, 16.5 mmol) in MeOH (150 mL) and H$_2$O (30 mL) was hydrogenated over 10% Pd/C (300 mg) at 40 psi fir 2.5 h. The reaction mixture was filtered and the filtrate concentrated in vacuo. The residue was recrystallized from MeOH (2X) to yield 7 (1.08 g, 40%) as an off-white crystalline solid. MP: 199–200° C. (dec). $^1$H NMR (D$_2$O):δ 3.94 (s, 2H). Anal calcd for C$_3$H$_7$N$_5$O.HCl: C, 21.82; H, 4.85; N, 42.42; Cl, 21.21. Found: C, 21.83; H, 4.91; N, 42.73; Cl, 21.36.

EXAMPLE 3

1,2,4-Triazine-3,6-dione, tetrahydro-, 3-hydrazone, monohydrochloride (Compound 9)

A soln of 8 (3.00 g, 20.4 mmol) in 1.0 M aq HCl (45 mL) was left standing at room temp for 24 h (NMR analysis of an aliquot indicated a 1:1 mixture of new products with no starting material remaining). The soln was then diluted to a total volume of 500 mL with THF. An oil separated. The mixture was chilled in an ice bucket for 1 h, whereupon some crystals appeared in the separated oil. Filtration of the mixture gave a white crystalline solid (0.86 g). NMR analysis indicated the solid was a 6:1 mixture of products 9:10 (major one having the upfield NMR signal). The oil in the filtrate continued to deposit crystals. After another hour, a second crop (0.55 g) was collected by filtration which was an 8:1 mixture of the same products. The second crop was dissolved in water (10 mL) and then diluted with THF (125 mL). The soln was left at 0° C. for 24 hrs, sonicated, and left at 0° C. for another 24 h. Filtration gave 87 mg of white crystals which consisted only of the major component 9 of the mixture (upfield NMR signal). $^1$H NMR (D$_2$O)δ 3.99 (s, 2 H); Anal. Calcd for C$_3$H$_7$N$_5$O.1 HCl: C, 21.76; H, 4.87; N, 42.30; Cl, 21.41. Found: C, 21.71; H, 4.77; N, 41.89; Cl, 21.60.

EXAMPLE 4

2,4-Imidazolidinedine, 3-amino-, 2-hydrazone, monohydrochloride (Compound 10)

A soln of 8 (2.20 g, 15.0 mmol) in 1.0 M aq HCl (33 mL) was allowed to stand at room temp. After 3 days, NMR analysis of an aliquot indicated two peaks at δ 4.3 and δ 4.0 in a ratio of 2:1, respectively. After 5 days, the ratio was 3:1, and at ten days the ratio was 5:1. At that time, the soln was diluted with THF (400 mL), whereupon an oil separated. The mixture was left at 0° C. for two days, at which time some crystals had appeared in the separated oil. The crystals were isolated by suction filtration and washed with THF. Drying in vacuo left white crystals (approx 400 mg), which were a 10:1 mixture of 10:9. $^1$H NMR (D$_2$O)δ 4.29 (s, 2 H); Anal. Calcd for C$_3$H$_7$N$_5$O. HCl: C, 21.76; H, 4.87; N, 42.30; Cl, 21.41. Found: C, 21.59; H, 5.01; N, 42.51; Cl, 21.25.

EXAMPLE 5

4-Imidazolidinone, 1,3-diamino-2-imino-, monohydrochloride (Compound 12)

Compound 11 (20.0 g, 135.9 mmol) was dissolved in 10% HCl (150 ml) and the resulting solution stirred overnight at ambient temperature. $^1$H NMR of an aliquot indicated the reaction had not gone to completion overnight. Concentrated aqueous HCl (2 ml) was added and the reaction monitored by $^1$H NMR. After 2 h the mixture was diluted with THF (800 ml) and the mixture stirred for 2 h in which time a solid precipitated. The solid was filtered and dried in vacuo to afford crude 4-imidazolidinone, 1,3-diamino-2-imino-, monohydrochloride as a mixture of two cyclic products in a 9:1 ratio. A portion of this material (0.50 g, 3.0 mmol) was recrystallized from H$_2$O/THF to afford 0.23 g pure 4-imidazolidinone, 1,3-diamino-2-imino-, monohydrochloride as a white crystalline solid. m.p. 209° C. (d). $^1$H NMR (D$_2$O)δ 4.29 (s, 2 H); $^{13}$C NMR (D$_2$O)δ 53.7, 159.6, 169.8. IR (mull) 3528, 3368, 3280 (b), 3251 (b), 3160 (b), 3111 (b), 3078 (b), 1775, 1757, 1713 (s), 1636, 1614, 1393, 1189, 638 cm$^{-1}$; MS (EI) m/z (rel. intensity) 129 (M+, 99), 130 (8), 129 (99), 101 (17), 100 (42), 85 (8), 58 (48), 57 (25), 56 (9), 55 (13), 45 (43). Anal. Calcd for C$_3$H$_8$ClN$_5$O. H$_2$O: C, 19.96; H, 5.47; N, 38.27; Found: C, 19.91; H, 5.47; N, 38.03.

Biological Testing

Compounds of the present invention were tested for their ability to reduce blood glucose and body weight as follows:

KKAy mice are rodent models of NIDDM and obesity (Chang, Wyse, Copeland, Peterson, and Ledbetter, 1986). A pre-treatment blood sample was obtained from the retro-orbital sinus and the mice arranged in groups of 5–6 so that the mean pre-treatment blood glucose level was the same on average in all groups. Test compounds were admixed in the chow at a concentration of 0.05–0.5% and the mice were allowed to consume the diet ad libitum. Control mice received unsupplemented chow. On Day 0, the mice were weighed and provided control chow or chow supplemented with test compounds. After 3 days of consuming control chow or chow supplemented with test compounds, a blood sample was obtained for determination of the glucose concentration and the animals were weighed for determination of weight loss. Food consumption was measured by weighing the food provided at the beginning of the study and the food residue at the end of the study. Food consumption was calculated by subtracting the weight of the residue from the weight of the food provided. Drug intake was calculated by multiplying food consumption by the concentration of drug in the diet. Using this method drug intake was determined to be approximately 62–444 mg of the free base form per kg per day. Blood glucose data are expressed as the average blood glucose concentration in the test group divided by the average blood glucose level in the control group (treatment/control or T/C). Compounds resulting in T/C values equal to or less than 0.90 are considered to be active antihyperglycemic agents. Weight loss data are expressed as percent change in body weight. Compounds resulting in a decrease of 0.22% or more less than control in body weight over three days are considered to be active anti-obesity agents. In a typical obese human subject (for example, a male, 68 inches in height and body mass index of 30) the loss of 0.22%/3 days would be equivalent to 1 pound per week (Bray, Endocrinology, 3rd edition, Chap. 143, p. 2627, 1995). A widely used clinical standard for satisfactory weight loss by obese humans is 1–2 pounds per week (Horton, Diabetes Mellitus Theory and Practice, 4th edition, Chapter 27, p. 461, 1990). Hence a drug that causes weight to be lost at the rate of 0.22%/3 days would be of benefit.

TABLE 1

Preferred Compounds of the Invention

| | | |
|---|---|---|
| 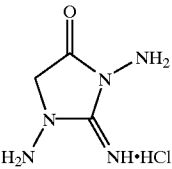 | 12 | 4-Imidazolidinone, 1,3-diamino-2-imino-, monohydrochoride |
| 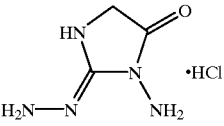 | 10 | 2,4-Imidazolidinedione, 3-amino-, 2-hydrazone, monohydrochloride |
| 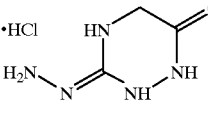 | 9 | 1,2,4-Triazine-3,6-dione, tetrahydro-, 3-hydrazone, monohydrochloride |

TABLE 2

Specifically Claimed Compounds of the Invention

| | | |
|---|---|---|
| 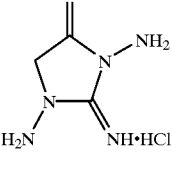 | 12 | 4-Imidazolidinone, 1,3-diamino-2-imino-, monohydrochloride |
| 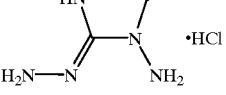 | 10 | 2,4-Imidazolidinedione, 3-amino-, 2-hydrazone, monohydrochloride |

TABLE 2-continued

Specifically Claimed Compounds of the Invention

| | | |
|---|---|---|
| 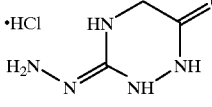 | 9 | 1,2,4-Triazine-3,6-dione, tetrahydro-, 3-hydrazone, monohydrochloride |
| 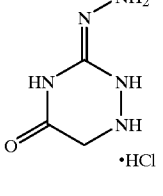 | 7 | 1,2,4-Triazine-3,5(2H, 4H)-dione, dihydro-, 3-hydrazone, monohydrochloride |
| 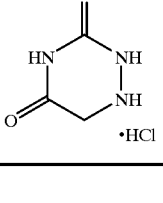 | 4 | 1,2,4-Triazin-5(2H)-one, 3-amino-1,6-dihydro-, monohydrochloride |

TABLE 3

Reduction in Hyperglycemia and Obesity in KKAy mice by Oral Administration of 4-Imidazolidinone, 1,3-Diamino-2-Imino-, Monohydrochloride

| Addition | Blood Glucose T/C | % Change Body Weight |
|---|---|---|
| 4-imidazolidinone, 1,3-diamino-2-imino-, monohydrochloride | | |
| 0.05% | 0.87 | −0.72 |
| 0.10% | 0.63 | −1.90 |
| 0.30% | 0.40 | −4.17 |
| 1-(hydrazinoiminomethyl) hydrazino-acetic | | |
| 0.05% | 0.63 | −1.75 |
| 0.10% | 0.39 | −3.74 |
| 0.30% | 0.30 | −6.68 |
| 3-GPA | | |
| 0.50% | 0.64 | −7.81% |

KKAy mice were treated with 4-imidazolidinone, 1,3-diamino-2-imino-, monohydrochloride described above except that the compound was admixed in the chow at 0.05, 0.10, and 0.30% so as to deliver daily doses of approximately 70, 125, and 400 mg/kg. Control mice received unsupplemented chow. For comparison to 4-imidazolidinone, 1,3-diamino-2-imino-, monohydrochloride, 3-guanidinopropionic acid (3-GPA) was administered as a 0.50% admixture in the chow (approximate dose, 700 mg/kg/day) and 1-(hydrazino-iminomethyl) hydrazino-acetic acid was administered as 0.05, 0.10, and 0.30% admixtures in the chow (approximate doses, 70, 100, and 320 mg/kg/day). Data are shown for the ratio for the mean blood glucose concentration in treated mice compared to control mice. The percent change in body weight on Day 3 is compared to Day 0 of the study.

TABLE 4

Reduction in Hyperglycemia and Obesity in KKAy mice by Oral Administration of Test Compounds

| Addition | Blood Glucose T/C | % Change Body Weight |
|---|---|---|
| 4-imidazolidinone, 1,3-diamino-2-imino-, monohydrochloride | 0.40 | −8.10 |

TABLE 4-continued

Reduction in Hyperglycemia and Obesity in KKAy mice by Oral Administration of Test Compounds

| Addition | Blood Glucose T/C | % Change Body Weight |
|---|---|---|
| 1,2,4-triazin-5(2H)-one, 3-amino-1,6-dihydro-, monohydrochloride | 1.08 | −2.30 |
| 1,2,4-triazine-3,5(2H,4H)-dione, dihydro-, 3-hydrazone, monohydrochloride | 1.00 | −0.24 |
| 1,2,4-triazine-3,6-dione, tetrahydro-, 3-hydrazone, monohydrochloride + 2,4-imidazolidinedione, 3-amino-, 2-hydrazone, monohydrochloride | 0.62 | −0.74 |

KKAy mice were treated with 4-imidazolidinone, 1,3-diamino-2-imino-, monohydrochloride; 1,2,4-triazin-5(2H)-one, 3-amino-1,6-dihydro-, monohydrochloride; 1,2,4-triazine-3,5(2H,4H)-dione, dihydro-, 3-hydrazone, monohydrochloride; or a mixture of 1,2,4-triazine-3,6-dione, tetrahydro-, 3-hydrazone, monohydrochloride and 2,4-imidazolidinedione, 3-amino-, 2-hydrazone, monohydrochloride as described above except that the compound was admixed in the chow at 0.10 (4-imidazolidinone, 1,3-diamino-2-imino-, monohydrochloride) or 0.50% 1,2,4-triazin-5(2H)-one, 3-amino-1,6-dihydro-, monohydrochloride; 1,2,4-triazine-3,5(2H,4H)-dione, dihydro-, 3-hydrazone, monohydrochloride, or the mixture of 1,2,4-triazine-3,6-dione, tetrahydro-, 3-hydrazone, monohydrochloride and 2,4-imidazolidinedione, 3-amino-, 2-hydrazone, monohydrochloride) so as to deliver daily doses of free base of approximately 89 and 440 mg/kg, respectively. Control mice received unsupplemented chow. Data are shown for the ratio for the mean blood glucose concentration in treated mice compared to control mice. The percent change in body weight on Day 3 is compared to Day 0 of the study.

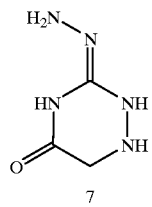

SCHEME 3

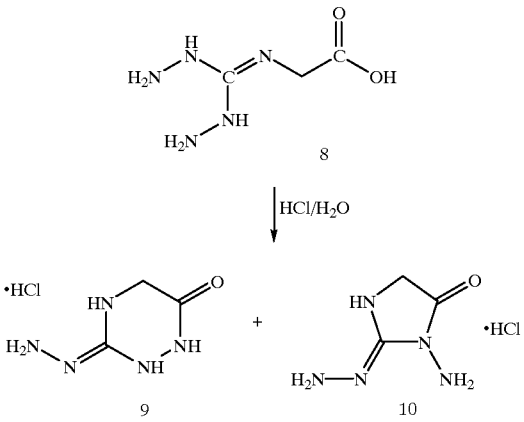

SCHEME 1

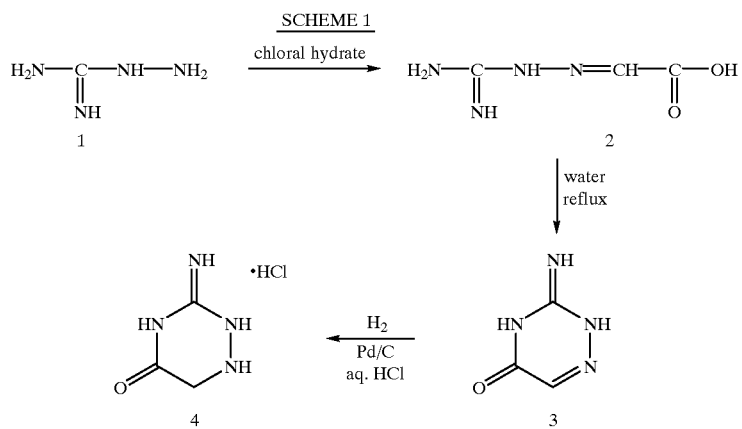

SCHEME 2

SCHEME 4

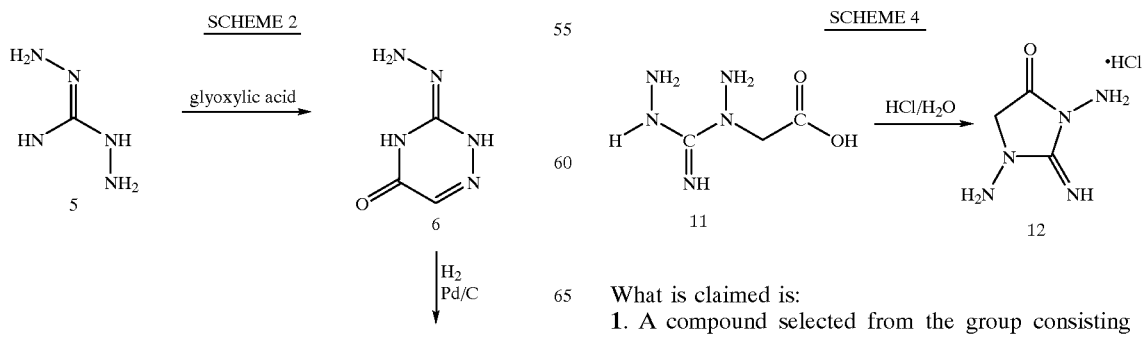

What is claimed is:
1. A compound selected from the group consisting of formulae III, IV, VI and VII

(III) 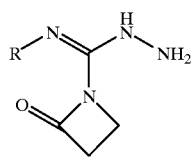

(IV) 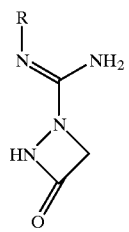

(VI) 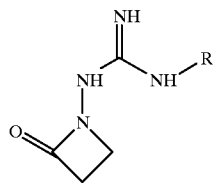

(VII) 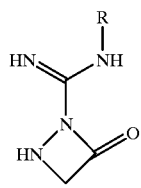

wherein R is H or $NH_2$, or a pharmacologically acceptable salt thereof.

2. A compound according to claim 1, of the formula III.
3. A compound according to claim 1, of the formula IV.
4. A compound according to claim 1, of the formula VI.
5. A compound according to claim 1, of the formula VII.
6. A method for treating non-insulin dependent diabetes mellitus (NIDDM) or obesity in a patient susceptible to or experiencing the NIDDM or obesity, comprising the systemic administration of a compound according to claim 1 in an amount effective to treat the NIDDM or obesity.
7. A method according to claim 6, wherein the compound is of formula III.
8. A method according to claim 6, wherein the compound is of formula IV.
9. A method according to claim 6, wherein the compound is of formula VI.
10. A method according to claim 6, wherein the compound is of formula VII.

* * * * *